US011353388B2

(12) United States Patent
Skaling (10) Patent No.: US 11,353,388 B2
(45) Date of Patent: *Jun. 7, 2022

(54) TIME-DOMAIN REFLECTOMETRY MATRIX SUCTION SENSOR

(71) Applicant: Whitney Skaling, Buellton, CA (US)

(72) Inventor: Whitney Skaling, Buellton, CA (US)

(*) Notice: Subject to any disclaimer, the term of this patent is extended or adjusted under 35 U.S.C. 154(b) by 282 days.

This patent is subject to a terminal disclaimer.

(21) Appl. No.: 16/776,342

(22) Filed: Jan. 29, 2020

(65) Prior Publication Data

US 2021/0231548 A1 Jul. 29, 2021

(51) Int. Cl.
*G01N 13/04* (2006.01)

(52) U.S. Cl.
CPC .................... *G01N 13/04* (2013.01)

(58) Field of Classification Search
CPC .................................................. G01N 13/04
USPC ................................................... 73/64.47
See application file for complete search history.

(56) References Cited

U.S. PATENT DOCUMENTS

| | | | |
|---|---|---|---|
| 3,430,486 A | 3/1969 | Richards | |
| 4,137,931 A | 2/1979 | Hasenbeck | |
| 5,898,310 A | 4/1999 | Liu | |
| 6,289,725 B1 | 9/2001 | Hubbell et al. | |
| 6,782,909 B1 | 8/2004 | Ragless | |
| 6,976,386 B1 | 12/2005 | Grover et al. | |
| 7,944,220 B2 | 5/2011 | Lock | |
| 8,058,885 B2 | 11/2011 | Caron | |
| 8,627,709 B2 | 1/2014 | Caron et al. | |
| 11,085,893 B2 * | 8/2021 | Skaling | G01N 27/225 |
| 2011/0057672 A1 | 3/2011 | Skaling | |
| 2018/0368339 A1 | 12/2018 | Van Der Lee | |

FOREIGN PATENT DOCUMENTS

| | | |
|---|---|---|
| EP | 0952444 A1 | 10/1999 |
| KR | 10-1502423 B1 | 3/2015 |

(Continued)

OTHER PUBLICATIONS

International Search Report, Application No. PCT/US2020/066363, pp. 1-11.

(Continued)

*Primary Examiner* — John Fitzgerald
*Assistant Examiner* — Rodney T Frank
(74) *Attorney, Agent, or Firm* — Lyon & Harr, LLP; Richard T. Lyon (57) ABSTRACT

A TDR matrix suction sensor measures the matrix suction exhibited by a porous medium surrounding the sensor. The sensor is constructed from a TDR matrix suction sensor probe, which includes two or more elongated conductors and a jacket that encases the conductors. The jacket is made of a hydrophilic, non-conductive, porous (HN-CP) material. In operation, a pulse delay time is computed for an electrical pulse injected into the proximal end of the conductors and reflected when reaching their distal ends. The pulse delay time and a delay-to-matrix suction profile of the HN-CP jacket material are used to compute the matrix suction exhibited by the probe jackets. An indicator of the current value of the matrix suction exhibited by the porous medium is then established based on the matrix suction computed for the HN-CP jackets.

20 Claims, 5 Drawing Sheets

(56) References Cited

FOREIGN PATENT DOCUMENTS

| WO | 1998004915 A1 | 2/1998 |
| WO | 2018-221051 A1 | 12/2018 |

OTHER PUBLICATIONS

International Preliminary Reporton Patentability, Application No. PCT/US2020/066363, dated Dec. 22, 2021, pp. 1-3.
PCT Demand and Amendment Under Article 34, Application No. PCT/US2020/066363, dated Jul. 17, 2021, pp. 1-18.

* cited by examiner

TIME-DOMAIN REFLECTOMETRY MATRIX SUCTION SENSOR

BACKGROUND

In the arts of soil science and hydrology, the hydraulic properties of various porous media are measured. Time-domain reflectometry (TDR) is a measurement technique which is used to measure a porous medium of interest. A TDR system generally includes a sensor which is disposed in the medium being tested and used to take the measurements. The measurements are then employed to determine the current properties of the media and optionally to monitor the media on an ongoing basis to detect changes in its properties. The media can be tested in situ (e.g., sensors can be disposed at different locations in a yard, farm field, process facility, or the like) or a sample of the media can be taken (such as a core sample and the like) and subsequently tested in a different setting such as a laboratory environment or the like.

The term "porous medium" refers to a medium which is composed of solids such as minerals and organic compositions, air and/or other gases, and one or more liquids, among other things. Exemplary types of porous media include soil (which may include materials such as sand, clay, sediments and organic matter), wood, rock, concrete, slurries of various sorts, foodstuffs, and grains, among other things.

The aforementioned measurements are subsequently analyzed in various ways for various purposes such as studying the efficiency of irrigation and drainage, optimizing the availability of water for plants, optimizing the yield of crops, and minimizing erosion. These measurements can also be used to follow the movement of liquids in porous media, model soil pore structure, and predict plant growth and other associated factors.

SUMMARY

This Summary is provided to introduce a selection of concepts, in a simplified form, that are further described hereafter in the Detailed Description. This Summary is not intended to identify key features or essential features of the claimed subject matter, nor is it intended to be used as an aid in determining the scope of the claimed subject matter.

Time-domain reflectometry (TDR) matrix suction sensor implementations described herein generally involve a sensor for measuring the matrix suction exhibited by a porous medium surrounding the sensor. In one implementation, the TDR matrix suction sensor includes a TDR matrix suction sensor probe disposed within the porous medium. The probe includes two or more elongated conductors and a jacket that encases the conductors. The jacket is made of a hydrophilic, non-conductive, porous (HN-CP) material. The TDR matrix suction sensor also includes TDR electronics. The TDR electronics are electrically connected to each probe conductor and computes a pulse delay time for an electrical pulse injected into the proximal end of the probe conductors and reflected when reaching a distal end thereof. In addition, there is a matrix suction computing device. The matrix suction computing device is in communication with the TDR electronics, and includes a matrix suction measuring computer program having a plurality of sub-programs executable by the matrix suction computing device. The sub-programs configure the matrix suction computing device to compute the matrix suction exhibited by the probe jacket based on the computed pulse delay time and a delay-to-matrix suction profile which defines the relationship between a pulse delay time value and the matrix suction exhibited by the HN-CP material of the probe jackets. The sub-programs also configure the matrix suction computing device to establish an indicator of the current value of the matrix suction exhibited by the porous medium based on the computed matrix suction exhibited by the HN-CP material of the probe jackets.

In another implementation, the TDR matrix suction sensor includes a TDR matrix suction sensor probe disposed within the porous medium. The probe includes two or more elongated conductors and a jacket that encases the conductors. The jacket is made of a HN-CP material. The TDR matrix suction sensor also includes TDR electronics. The TDR electronics are electrically connected to a proximal end of each probe conductor and inject an initial electrical pulse into the proximal end thereof. The TDR electronics also record the time of injection and detect the arrival of a reflected pulse generated when the initial pulse is reflected upon reaching a distal end of the probe conductors. The time of arrival is also recorded. In addition, there is a matrix suction computing device. The matrix suction computing device is in communication with the TDR electronics, and includes a matrix suction measuring computer program having a plurality of sub-programs executable by the matrix suction computing device. The sub-programs configure the matrix suction computing device to compute a pulse delay time based on the injection time of the initial pulse and the arrival time of the reflected pulses. In addition, the sub-programs compute the matrix suction exhibited by the probe jacket based on the computed pulse delay time and a delay-to-matrix suction profile which defines the relationship between a pulse delay time value and the matrix suction exhibited by the HN-CP material of the probe jacket. The sub-programs further configure the matrix suction computing device to establish an indicator of the current value of the matrix suction exhibited by the porous medium based on the computed matrix suction exhibited by the HN-CP material of the probe jackets.

Another exemplary implementation involves a computer-implemented process for measuring the matrix suction exhibited by a porous medium. This process includes using one or more computing devices that are in communication with each other to perform the following process actions. An initial electrical pulse is first injected into conductors at a proximal end of a TDR matrix suction sensor probe disposed within the porous medium. The probe includes two or more elongated conductors and a jacket that encases the conductors. The jacket is made of a HN-CP material. The time the initial electrical pulse was injected is recorded. In addition, the arrival of a reflected electrical pulses generated when the initial pulse is reflected upon reaching a distal end of the probe conductors is detected. The time of arrival of the reflected electrical pulses is also recorded. A pulse delay time based on the injection time of the initial pulse and the arrival time of the reflected pulses is then computed, and the matrix suction exhibited by the HN-CP material of the probe jacket is also computed. The matrix suction exhibited by the HN-CP jacket material is computed based on the pulse delay time and a delay-to-matrix suction profile which defines the relationship between a delay and the matrix suction exhibited by the HN-CP probe material. An indicator of the current value of the matrix suction exhibited by the porous medium is established next based on the matrix suction computed for the HN-CP material of the probe jackets.

DESCRIPTION OF THE DRAWINGS

The specific features, aspects, and advantages of the TDR matrix suction sensor implementations described herein will become better understood with regard to the following description, appended claims, and accompanying drawings where:

FIG. 2A-B are diagrams illustrating an exemplary implementation, in simplified form, of a TDR matrix suction sensor probe for measuring the matrix suction of a porous medium surrounding the sensor.

DETAILED DESCRIPTION

In the following description reference is made to the accompanying drawings which form a part hereof, and in which are shown, by way of illustration, specific implementations in which a TDR matrix suction sensor can be practiced. It is understood that other implementations can be utilized and structural changes can be made without departing from the scope of the TDR matrix suction sensor.

It is also noted that for the sake of clarity specific terminology will be resorted to in describing the TDR matrix suction sensor implementations described herein and it is not intended for these implementations to be limited to the specific terms so chosen. Furthermore, it is to be understood that each specific term includes all its technical equivalents that operate in a broadly similar manner to achieve a similar purpose. Reference herein to "one implementation", or "another implementation", or an "exemplary implementation", or an "alternate implementation", or "some implementations", or "one tested implementation"; or "one version", or "another version", or an "exemplary version", or an "alternate version", or "some versions", or "one tested version"; or "one variant", or "another variant", or an "exemplary variant", or an "alternate variant", or "some variants", or "one tested variant"; means that a particular feature, a particular structure, or particular characteristics described in connection with the implementation/version/variant can be included in one or more implementations of the TDR matrix suction sensor. The appearances of the phrases "in one implementation", "in another implementation", "in an exemplary implementation", "in an alternate implementation", "in some implementations", "in one tested implementation"; "in one version", "in another version", "in an exemplary version", "in an alternate version", "in some versions", "in one tested version"; "in one variant", "in another variant", "in an exemplary variant", "in an alternate variant", "in some variants" and "in one tested variant"; in various places in the specification are not necessarily all referring to the same implementation/version/variant, nor are separate or alternative implementations/versions/variants mutually exclusive of other implementations/versions/variants. Yet furthermore, the order of process flow representing one or more implementations, or versions, or variants does not inherently indicate any particular order nor imply any limitations of the TDR matrix suction sensor.

As utilized herein, the terms "module", "component," "system," "client" and the like can refer to a computer-related entity, either hardware, software (e.g., in execution), firmware, or a combination thereof. For example, a component can be a process running on a processor, an object, an executable, a program, a function, a library, a subroutine, a computer, or a combination of software and hardware. By way of illustration, both an application running on a server and the server can be a component. One or more components can reside within a process and a component can be localized on one computer and/or distributed between two or more computers. The term "processor" is generally understood to refer to a hardware component, such as a processing unit of a computer system.

Furthermore, to the extent that the terms "includes," "including," "has," "contains," and variants thereof, and other similar words are used in either this detailed description or the claims, these terms are intended to be inclusive, in a manner similar to the term "comprising", as an open transition word without precluding any additional or other elements.

1.0 Introduction

In general, the TDR matrix suction sensor implementations described herein are employed to measure the matrix suction exhibited by a porous medium. Matrix suction is a measurement of the adhesive pressures exerted by water or other liquid within the pore structure of a porous media that by nature tends to be in equilibrium with its surrounding media. This is useful, for example, in estimating how much energy a plant would need to expend to draw moisture from the soil surrounding its roots, and therefore how much water should be added to the soil to minimize the energy the plant needs to expend.

More particularly, plants extract water from the soil surrounding their roots. As water is extracted from the voids in the porous soil adjacent the plant's roots, the remaining water molecules in the voids are held to the soil particle surfaces more tightly. The more tightly held water molecules exert a higher resistive force against the plant roots' suction force that draws in the water from the soil. The more water that is extracted, the larger the suction force must become as the water molecules cling more and more closely to the soil particle surfaces. Thus, it becomes harder and harder for the plant to extract more water. The suction force is often referred to as the matrix potential or matrix suction. It has been estimated in the past that the ideal matrix suction range for optimum plant health is between about −10 to −50 centibars.

Different soil types will produce a similar matrix suction value at very different volumetric soil moisture values. For example, at one extreme, soil primarily made up of fine sand can exhibit a matrix suction in the ideal range when its volumetric moisture content is well below 10 percent. Whereas, at the other extreme, soil primarily made up of clay may need a volumetric moisture content of up to 40 percent to exhibit a matrix suction in the ideal range. In view of this, a sensor that measures the matrix suction of soil (as does the TDR matrix suction sensor implementations described herein), has an advantage over volumetric sensors that just measure the soil moisture as a percentage of soil volume. Namely, a matrix suction sensor can be used in an unknown type of soil and still provide an indication of the pore water environmental soil conditions with regard to maximizing plant health and minimizing stress conditions within the soil-water matrix.

It is noted that while the use of the TDR matrix suction sensor implementations described herein is advantageous in measuring the matrix suction exhibited by soil, it is not intended that the sensor implementations be limited to measuring soil. Rather, any porous medium (e.g., wood, rock, concrete, slurries of various sorts, foodstuffs, and grains, among other things) that exhibits a matrix suction effect when a liquid is introduced can be measured using the TDR matrix suction sensor implementations described herein.

2.0 TDR Matrix Suction Sensor and Environment

Figure 1:
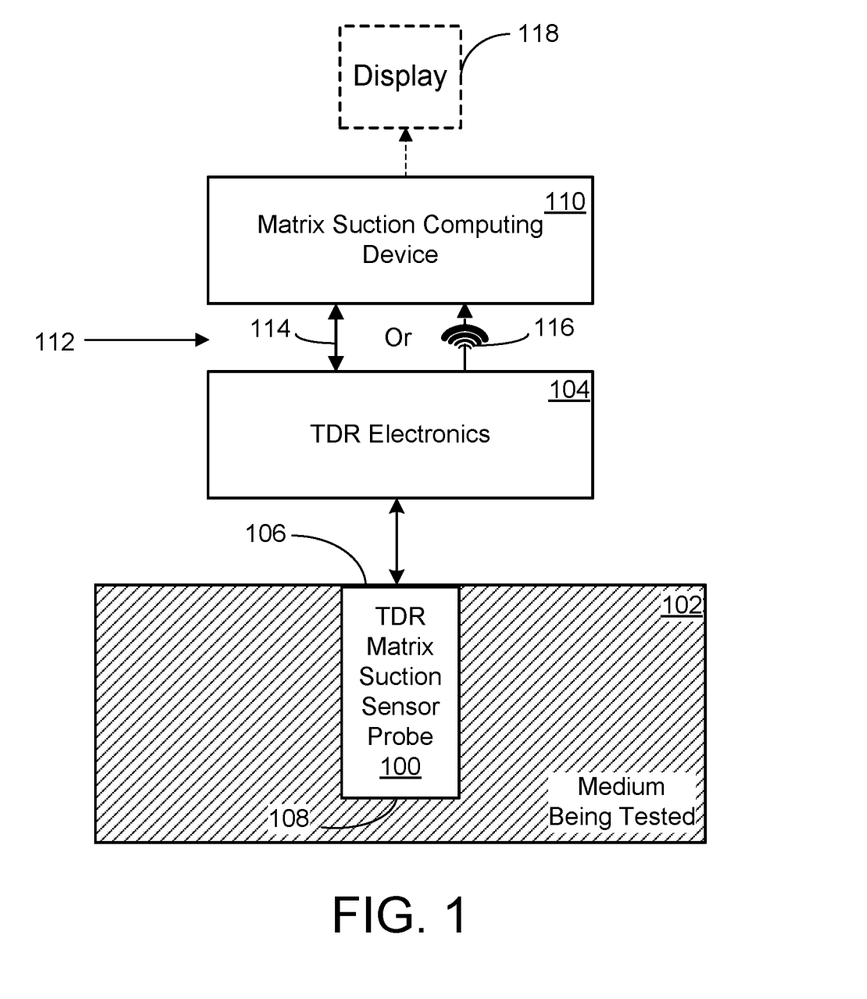
FIG. 1 is a diagram illustrating an exemplary implementation, in simplified form, of a suitable environment for realizing the TDR matrix suction sensor implementations described herein.

FIG. 1 illustrates a simplified exemplary environment in which the TDR matrix suction sensor implementations described herein can be employed. The environment illustrated in FIG. 1 is only one example of a suitable environment and is not intended to suggest any limitation as to the scope of use or functionality of the TDR matrix suction sensor implementations. Neither should the environment be interpreted as having any dependency or requirement relating to any one or combination of the components discussed hereafter.

As exemplified in FIG. 1, a suitable environment for implementing the TDR matrix suction sensor implementations described herein generally includes the following components. A TDR matrix suction sensor probe 100 is disposed within a porous medium 102 which is being measured. Time-domain reflectometry (TDR) electronics 104 are electrically connected to the proximal end 106 of the probe 100. The TDR electronics 104 interoperate with the probe 100 to test the medium 102. Typically, the TDR electronics 104 generally include a signal generator component (not shown), a signal detector component (not shown) and a signal processor component (not shown) whose operation will be described in more detail hereafter.

Referring again to FIG. 1, the TDR electronics 104 interoperate with the TDR matrix suction sensor probe 100 as follows. The signal generator component injects an initial short rise-time, short duration electrical pulse (e.g., broadband, stepped, impulse, or a combination pulse) into the proximal end 106 of the probe 100 and into the signal processor component, which records the time the initial pulse was injected. Generally speaking, the pulse is sent into each of the probe's conductors 100 which operate as transmission line (also known as a "wave guide" or "antenna") and provides a means for the initial electrical pulse and a resulting reflected electrical pulses to propagate along the probe conductors as follows. The initial electrical pulse propagates from the proximal end 106 of the probe 100, down each of the conductors toward the distal end 108 of the probe. The conductors at the distal end 108 of the probe 100 are un-terminated so that when the initial pulse reaches the distal end of each conductor, the original pulse is reflected, thus generating the reflected electrical pulses which propagates from the distal end of the probe back toward the proximal end 106 of the probe. When the reflected pulses reaches the proximal end 106 of the probe 100, they are received by the signal detector component. The signal detector component then informs the signal processor component of the times the reflected pulses arrived. Generally speaking, the signal processor component then computes an overall arrival time from the reflected pulses arrival times, and compares it to the injected initial pulse to determine an average travel time (which is also referred to as the pulse phase delay or just delay for short).

In typical TDR systems designed to determine the moisture content of the material being measured, the delay time is employed to ascertain the apparent dielectric constant of the material using the travel times through the material. More particularly, it is known that the velocity of propagation through a medium is proportional to the dielectric of the medium. When the probes are inserted in material being measured, the material, together with the probes, act as an electronic circuit. The transmission speed of a pulse in the probes is affected primarily by the water content of the material being measured. As water content increases in the measured material, so also does the travel time of the pulse reaching a reflected end point from the probe beginning. The delay time from beginning to end as observed in TDR wave form features will determine the apparent dielectric of the material being measured. Thus, there is a relationship between the apparent measured dielectric constant and the moisture content of the measured material. In typical TDR systems, once the apparent dielectric constant is determined from propagation velocity, the volumetric soil moisture is computed or deduced.

However, in one TDR matrix suction sensor implementation, while the TDR electronics 104 operate in the same manner as described previously to determine the pulse delay time, the TDR matrix suction sensor probe 100 (which will be described in more detail in sections to follow) is employed instead of traditional TDR probes, and a matrix suction computing device 110 operates to determine a matrix suction value for the material being measured from the pulse delay time in lieu of the moisture content of the material.

The matrix suction computing device 110 is connected to the TDR electronics 104 via connection path 112. In one implementation, the TDR electronics 104 and matrix suction computing device are part of an integrated unit and are directly connected to each other (such as via a wired connection 114). In another implementation, the connection path 112 takes the form of a wireless transmission device (not shown) that wirelessly transmits a signal 116 from the TDR electronics 104 to the matrix suction computing device 110. It is noted that for the purposes of this description, the term wireless refers to any communication scheme not involving a connection via an electrical conductor, including radio frequency (e.g., near field communication (NFC), bluetooth, microwave and so on) and optical (e.g. infrared (IR), ultraviolet (UV) and visible light communication (VLC)). Additionally, the wireless communication can involve a direct communication path (e.g., two-way), or via a computer network (e.g., internet, intranet, and so on). In this latter implementation, the matrix suction computing device 110 is a separate stand-alone unit. It is noted that in either the foregoing wired or wireless configurations, the TDR electronics 104 can compute the pulse phase delay as is the case with current TDR systems. In this case, it is the pulse phase delay that is provided to the matrix suction computing device 110 (such as in the signal 116). Alternately, the TDR electronics 104 can simply provide the time the original pulse was transmitted and the time the reflected pulse was detected to the matrix suction computing device either via a wired or wireless connection. In this latter case, the matrix suction computing device computes the pulse phase delay.

In one implementation, the matrix suction computing device 110 also includes a display device 118. The optional nature of the display device 118 is shown in FIG. 1 by the use of a broken line box. The display device 118 is employed to display an indicator of the current value of the matrix suction exhibited by the porous medium surrounding the sensor.

2.1 TDR Matrix Suction Sensor Probe

Figure 2A:
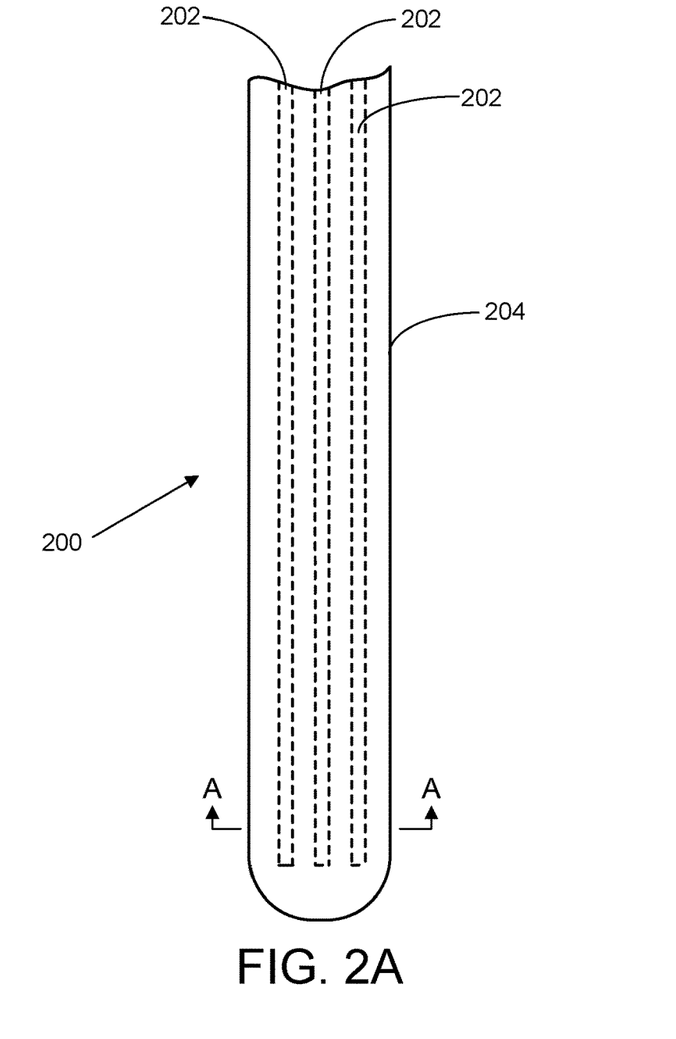
Figure 2B:
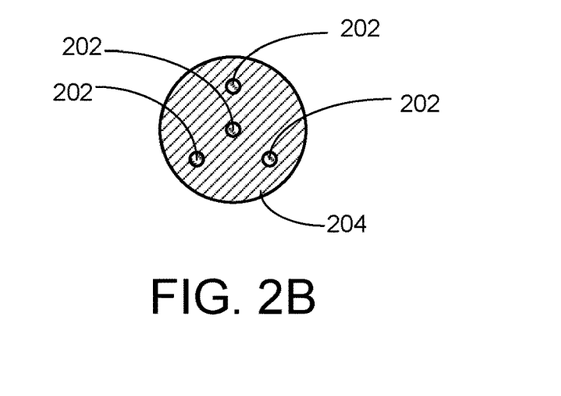
FIG. 2B illustrates a cross-sectional view, in simplified form, of the sensor probe of FIG. 2A taken along line A-A of FIG. 2A.

Referring to FIGS. 2A-B, in one implementation, the TDR matrix suction sensor probe 200 includes elongated conductors 202 and a jacket 204 that encases the conductors. The conductors 202 run along the longitudinal axis of the probe 200 and can be constructed from any material which is electrically conductive. By way of example but not limitation, the conductors 202 can be constructed from a variety of different metals such as copper, brass, stainless steel, nickel alloys, aluminum, gold, platinum, silver, and the like. The conductors 202 can also be constructed by sintering a powdered form of these metals, or the conductors 202 can be formed as a composite material using vapor deposition, liquid deposition, or flame deposition of any of these metals on top of a non-conductive material. The conductors 202 can further be in the form of a hollow tube.

The conductors 202 is electrically active and used as transmission elements for the aforementioned pulses. To this end, the proximal end 206 of each conductor 202 is connected to the aforementioned TDR electronics. In the TDR matrix suction sensor probe implementation exemplified in FIGS. 2A-B, each conductor 202 has an axial interior that is solid and a radial cross-sectional shape that is circular. A variety of alternate versions of the conductors (not shown) are also possible. By way of example, but not limitation, the conductors can also have any other radial cross-sectional shape. For instance, the conductors can have a radial cross-sectional shape that is oval, triangular, square, rectangular, pentagonal, hexagonal, octagonal, or star, among others.

The jacket 204 that encases the conductors 202 is made of a hydrophilic, non-conductive, porous material (which will be abbreviated as a HN-CP material for the purposes of this description). For example, the HN-CP material can be a porous ceramic (e.g., a high flow alumina-based ceramic), porous plastic, or the like. This HN-CP material has a continuous, interconnected system of pores which is permeable to liquids, gasses and various combinations thereof. The pores in the HN-CP material have a known distribution throughout, and a known size distribution. The pore structure of a given HN-CP material can be specified in terms of an air entry value (which is commonly measured using a unit of "bubbling pressure" known as a "bar"). When the porous media being measured is soil and the liquid being pulled in and out of the HN-CP material is water, in one implementation, the HN-CP jacket is made of a porous material having a 0.5 to 1.0 bar pore structure. This bar structure has the advantage of not losing water at a potentially unacceptable rate when the soil being measured dries and pulls the water from the HN-CP jacket. However, it is not intended to limit the HN-CP jacket to a ceramic or plastic material, or to the just-stated pore structure. Other materials and pore structures may be employed as needed to accurately determine the matrix suction of the media being measured.

Since the HN-CP material is hydrophilic, it has an advantage in that a polar liquid (such as water) from the surrounding porous media being measured is "wicked" into the pores of the HN-CP material. In other words and generally speaking, the liquid is naturally pulled from the media being measured and flows into the pores of the HN-CP material (or is pulled from the pores of the HN-CP material and flows back into the media being measured as the case may be) until an equalization in the matrix suction exhibited by the HN-CP material and the surrounding porous material being measured is achieved.

The HN-CP jacket 204 can be mass produced with very consistent and uniform pore structures throughout, thus making the aforementioned matrix suction measurements possible (as will be described in the sections to follow). Further, the HN-CP jacket is very durable and generally inert. Thus, the HN-CP jacket will not degrade or change its porosity properties when salt or other minerals or chemicals are present in the media being measured.

Referring again to the implementation shown in FIGS. 2A-B, the HN-CP jacket 204 that surrounds the conductors 202 has a radial cross-sectional circular shape with a dome-shaped distal end. The HN-CP jacket 204 can be formed as a single piece that slides over the conductors 202, or in two or more pieces (not shown) as desired. In implementations where the jacket is made of more than one piece, it is bonded together to form a single unit that surrounds the sensing body. It is believed the bonding lines in the jacket will have a negligible effect on the sensor readings. Further, the HN-CP jacket could be formed around the conductors. Regardless of how the jacket is formed, the resulting structure has interior cavities that accommodate the conductors and conform to the shape of the conductors, such that the walls of each jacket cavity contacts a conductor across its exterior surface without forming any significant gaps where liquid could pool (thereby adversely affecting the readings).

The TDR matrix suction sensor implementations described herein are not limited to the circular cross-sectional shaped HN-CP jacket shown in FIGS. 2A-B. Rather, it is believed any practical shape is possible without significantly affecting the matrix suction measurements. For example, other HN-CP jacket shapes (not shown) include, but are not limited to, jackets having a radial cross-sectional circular shape with a pointed, conical-shaped distal end, or jackets having a radial cross-sectional shape forming a rectangle, or a square, or a triangular, or an oval, or a pentagon, or a hexagon, or an octagon, or a star, among others. In any of these alternative cross-sectional shapes, the exterior of the jacket can have a pointed distal end to facilitate its insertion into the porous medium being measured.

It is further noted that the HN-CP material of TDR matrix suction sensor jacket has a delay-to-liquid content profile which defines the relationship between the aforementioned pulse phase delay as measured by the TDR electronics and the amount of liquid held within the HN-CP jacket material. As the liquid content varies within the HN-CP material, the dielectric nature of the material will change. More particularly, as is appreciated in the art of electromagnetism, the relative permittivity (also known as the dielectric constant) of a material specifies a measure of the material's ability to transmit (i.e., "permit") an electric field. Generally speaking, the relative permittivity of a HN-CP material changes in conjunction with changes in the amount of liquid which is present within the material. In other words, as liquid flows from the medium being measured into the pores of the HN-CP material, the relative permittivity of the material increases. Correspondingly, as liquid flows from the HN-CP material back into the medium, the relative permittivity of the ceramic material decreases. These changes in the relative permittivity of the ceramic material affect the original and reflected electrical pulses. More particularly, as the liquid content of the porous HN-CP material increases, the velocity of the original electrical pulse as it propagates along each of the TDR matrix suction sensor probes toward its distal end decreases, and the velocity of the reflected electrical pulse as it propagates along the probe back toward its proximal end similarly decreases. Correspondingly, as the liquid content of the HN-CP material decreases the velocity of the original pulse as it propagates along each of the sensor probes toward its distal end increases, and the velocity of the reflected pulse as it propagates along the probe back toward its proximal end similarly increases.

The HN-CP jacket material also exhibits a known liquid-release curve (also referred to in the arts of hydrology and soil science as a "moisture-release curve" or a "moisture-retention curve") due to the fact that the pores have a known distribution throughout the ceramic material, and the fact that the pores have a known size distribution. As is appreciated in the hydrology and soil science arts, the liquid-release curve of a material defines the relationship between the liquid content and the matrix suction (or liquid potential) of the material.

In view of the foregoing, it can be appreciated that there is a quantifiable relationship between the pulse phase delay and the matrix suction exhibited by the HN-CP material of TDR matrix suction sensor jacket. This relationship will sometimes be referred to herein as the delay-to-matrix suction profile of the HN-CP jacket material. Further, when the HN-CP jacket material is in equilibrium with the surrounding medium being measured (as described previously), the matrix suction exhibited by the HN-CP material is equal to the matrix suction exhibited by the porous medium surrounding the TDR matrix suction sensor. Thus, by measuring the pulse phase delay once equilibrium is reached, the matrix suction exhibited by the porous medium surrounding the TDR matrix suction sensor can be ascertained based on the delay-to-liquid content profile and liquid-release curve of the HN-CP material. In general, the previously described TDR electronics are used to measure the pulse phase delay, while the matrix suction computing device is employed to compute the matrix suction exhibited by the porous medium surrounding the TDR matrix suction sensor.

The delay-to-liquid content profile and liquid-release curve of the HN-CP jacket material is determined using standard methods. For example, since the jacket is made from a porous material with known characteristics (porosity, pore distribution, etc.), a water-retention curve can be created using the any of several well-known models (such as the van Genuchten model). In view of the foregoing, it is possible to construct an algorithmic matrix suction formulation that can be used compute the matrix suction of the porous medium being measured directly. Alternatively, this formulation can be employed to construct a lookup table that provides the jacket's matrix suction for each of a series of delay times.

Referring again to FIGS. 2A-B, the illustrated probe implementation has a 4-conductor configuration with a central conductor and three equally spaced conductors surrounding the central conductor. This is a typical configuration of the conductive probes associated with many existing TDR sensors. However, TDR sensors also have other conductor configurations. In general, a TDR sensor has two or more conductors. The configuration and number of conductors in the TDR matrix suction sensor probe implementations described herein can mimic the configuration and number of probes in existing TDR sensors. Thus, a TDR matrix suction sensor probe as described herein will have two or more conductors. Further, it is possible to use the conductive probes and TDR electronics of an existing TDR sensor to create a TDR matrix suction sensor by encasing the conductors in the aforementioned HN-CP jacket and adding a matrix suction computing device. However, even though a TDR matrix suction sensor can employ parts of an existing TDR sensor, they operate differently. One significant difference is that in a typical TDR sensor, its conductive probes are inserted into the porous medium being measured such that the conductive probes are surrounded and separated by the medium itself. Whereas, in the TDR matrix suction sensor probe described herein, its conductors are disposed within the HN-CP jacket, such that the conductors are surrounded and separated by the jacket material—not the porous medium being measured. Rather, the porous medium surrounds the exterior of the jacket instead. This difference is significant because the probes in a typical TDR sensor are employed to directly measure the moisture content of the porous medium they are inserted into, as described previously. On the other hand, the TDR matrix suction sensor is employed to measure the matrix suction exhibited by the HN-CP material of the sensor jacket. It does not directly measure the surrounding porous medium. In fact, the configuration of the HN-CP jacket is made to minimize the effect the surrounding porous medium has on the aforementioned pulses. To accomplish this, the field generated when the conductors are energized by the pulses should not significantly extend outside the confines of the HN-CP jacket. This ensures that the porous medium surrounding the TDR matrix suction sensor probe does not contribute in a meaningful way to the pulse delay. Several factors determine the extent of the "pulse field". The material used for the conductors, their cross-sectional area and their length all play a part. In addition, the power of the pulses plays a part. And further, the type of HN-CP material used for the jacket and the jacket's cross-sectional area (in particular, the minimum distance between a conductor and the exterior surface the jacket) also play a part. These factors are balanced in order to minimize the effect the surrounding porous medium has on the pulse delay. It is noted that if an existing TDR sensor is employed to construct the TDR matrix suction sensor, the foregoing factors associated with the conductors and pulses will already be established. Thus, the type of HN-CP material used for the jacket and the jacket's cross-sectional area would be made such that the pulse field is substantially confined within the jacket.

2.2 Matrix Suction Computing Device System Framework

Figure 3:
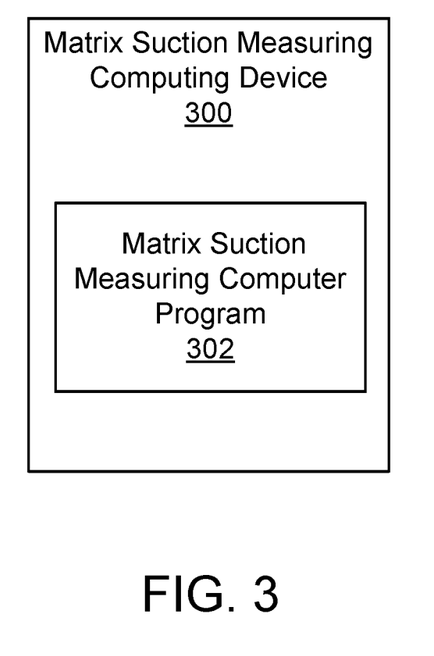
FIG. 3 is a diagram illustrating one implementation, in simplified form, of a system framework for measuring the matrix suction of a porous medium surrounding the TDR matrix suction sensor using the matrix suction computing device.

FIG. 3 illustrates one implementation, in simplified form, of a system framework for measuring the matrix suction of a porous medium surrounding a TDR matrix suction sensor using the matrix suction computing device. As exemplified in FIG. 3, the system framework includes a matrix suction measuring computer program 302 running on the matrix suction computing device 300. The matrix suction measuring computer program 302 has a plurality of sub-programs executable by the computing device.

Figure 4:
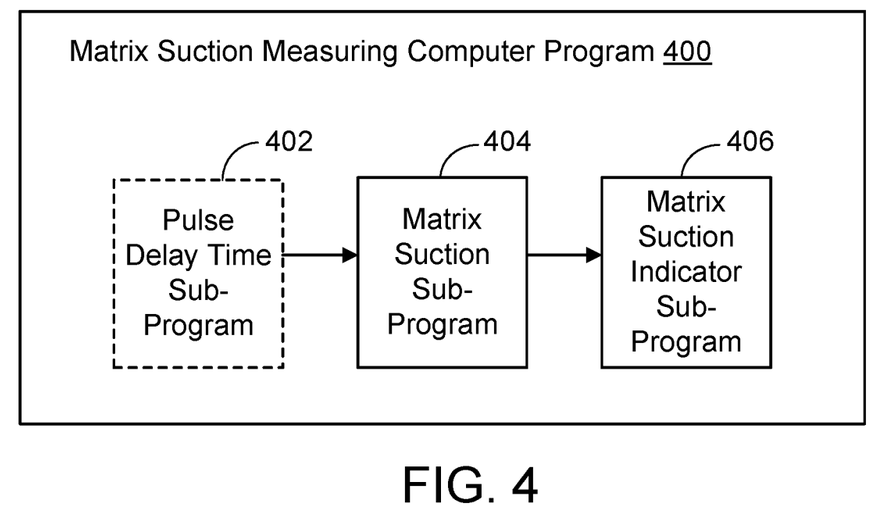
FIG. 4 is a diagram illustrating one implementation, in simplified form, of sub-programs included in the matrix suction measuring computer program.

FIG. 4 illustrates one implementation, in simplified form, of sub-programs included in the matrix suction measuring computer program 400 that configure the aforementioned matrix suction computing device. More particularly, an optional pulse delay time computation sub-program 402 is included as shown in FIG. 4. The pulse delay time computation sub-program 402 is optional in that it is employed in an implementation where the TDR electronics provides the recorded pulse events to the matrix suction computing device which then computes the pulse delay time. This optional sub-program 402 is not employed in an alternative implementation where the TDR electronics computes the pulse delay time from the recorded pulse events and provides it to the matrix suction computing device. The optional nature of the pulse delay time computation sub-program 402 is indicated by the use of a broken line box in FIG. 4. The matrix suction measuring computer program 400 also includes a matrix suction computation sub-program 404 that computes the matrix suction exhibited by the HN-CP material of the jacket based on the pulse delay time and the delay-to-matrix suction profile which defines the relationship between a delay and the matrix suction exhibited by the material. The matrix suction indicator sub-program 406 then establishes an indicator of the current value of the matrix suction exhibited by the porous medium surrounding the sensor based on the matrix suction computed for the HN-CP material of the jacket.

2.3 Process for Measuring Matrix Suction

Figure 5:
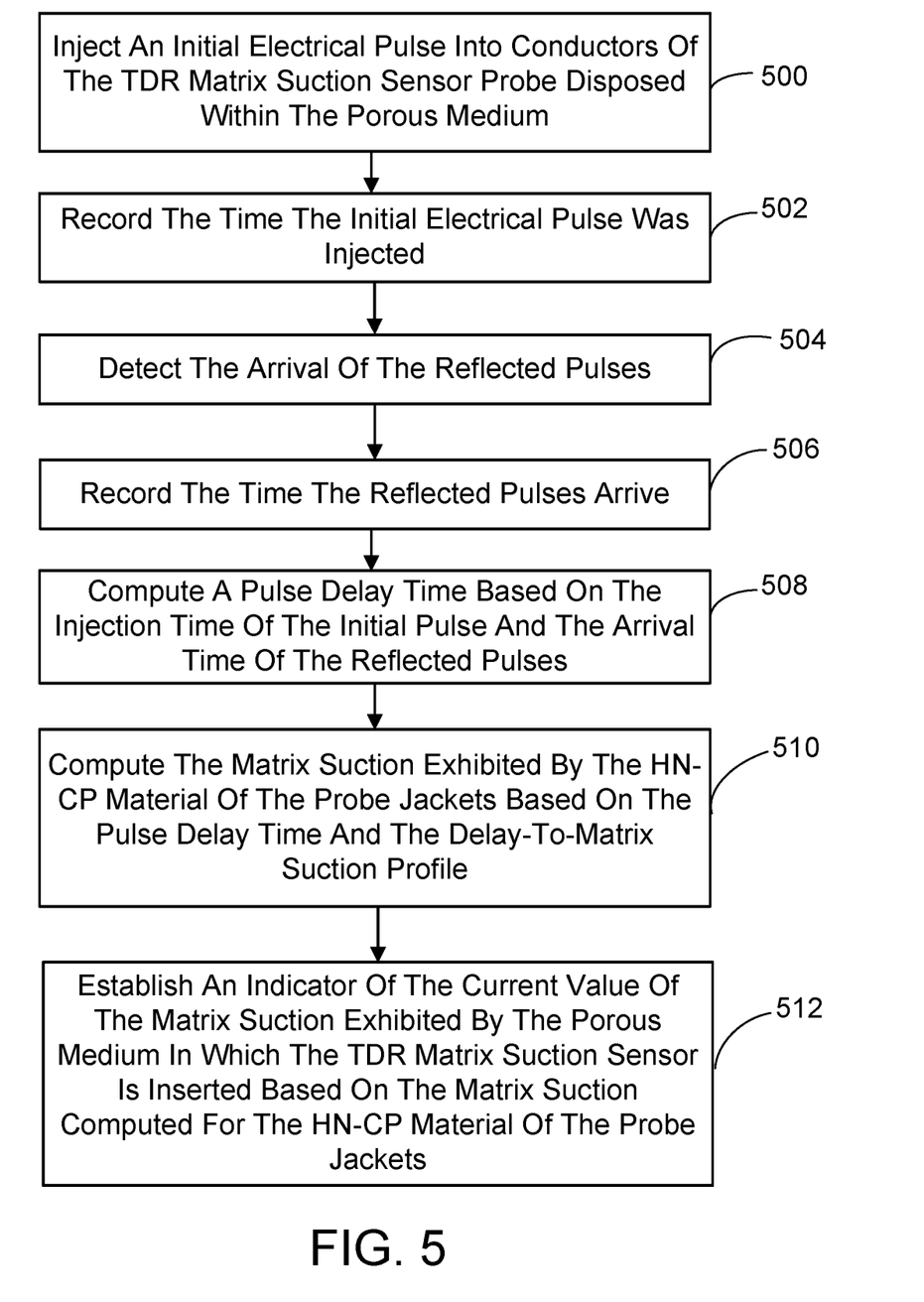
FIG. 5 is a flow diagram illustrating an exemplary implementation, in simplified form, of a process for measuring the matrix suction of a porous medium surrounding a TDR matrix suction sensor.

FIG. 5 illustrates an exemplary implementation, in simplified form, of a process for measuring the matrix suction exhibited by a porous medium surrounding the TDR matrix suction sensor probe based on the above-described matrix suction measuring computer program as realized on one or more computing devices. As exemplified in FIG. 5, the process starts with injecting an initial electrical pulse via the previous described TDR electronics into the conductors at a proximal end of a TDR matrix suction sensor probe disposed within the porous medium (process action 500). As described previously, the probe includes two or more elongated conductors and a jacket that encases the conductors, where the jacket is made of a HN-CP material. The time the initial electrical pulse was injected is recorded (process action 502). The pulse propagates down the conductors of the TDR matrix suction sensor probe and reflected pulses are created when the initial pulse reaches the distal end of the probe conductors as described previously. The TDR electronics then detects the arrival of the reflected pulses (process action 504) and records a time of arrival (process action 506). A pulse delay time is then computed based on the injection time of the initial pulse and the arrival time of the reflected pulses (process action 508). It is noted that in one implementation, the TDR electronics computes the pulse delay time from the recorded pulse events and provides it to the matrix suction computing device. In an alternative implementation, the TDR electronics provides the recorded pulse events to the matrix suction computing device which then computes the pulse delay time. In one implementation, the matrix suction exhibited by the HN-CP material of the probe jacket is computed next by the matrix suction computing device based on the pulse delay time and the delay-to-matrix suction profile which defines the relationship between a delay and the matrix suction exhibited by the HN-CP probe material (process action 510). An indicator of the current value of the matrix suction exhibited by the porous medium in which the TDR matrix suction sensor is inserted is then established based on the matrix suction computed for the HN-CP material of the probe jackets (process action 512).

2.4 TDR Matrix Suction Sensor Operation

One exemplary environment for operating the TDR matrix suction sensor implementations described herein generally includes the following. A TDR matrix suction sensor probe is disposed within a porous medium which is being measured. More particularly, the TDR matrix suction sensor probe is disposed in the media such that the outer surface of the probe jacket comes into contact with and is surrounded by the porous media. For example, the TDR matrix suction sensor can be used to measure the matrix suction of soil. In this scenario, the sensor probe is inserted into the soil, either by driving the probe into the soil if the soil is loose enough not to damage the probe or is interference-fit into a pre-made hole in the soil.

In general, the HN-CP jacket of the sensor probe provides a means for absorbing a liquid from the porous media it is in contact with. In other words, since the outer surface of the HN-CP jacket is exposed to the porous media being measured, the jacket maintains fluid contact with the media. This allows for fast transfer of liquid (e.g., water) from the media being measured (e.g., soil) to the HN-CP jacket until the matrix suction exhibited by media being measured and that being exhibited by the HN-CP jacket equalize, and also allows this equalization to be continuously maintained as the liquid content within the surrounding media changes. In other words, when the TDR matrix suction sensor probe is first introduced into a porous material, its HN-CP jacket pulls in liquid from the surrounding porous material into the jacket material until an equilibrium between the jacket matrix suction and the surrounding material's matrix suction is reached. This is the case when the liquid content of the HN-CP material produces a lower matrix suction than exhibited by the surrounding porous medium. Alternatively, if the liquid content of the HN-CP material produces a higher matrix suction than exhibited by the surrounding porous medium, when the TDR matrix suction sensor probe is first introduced into the porous material, its HN-CP jacket releases liquid into the surrounding porous material until an equilibrium between the jacket matrix suction and the surrounding material's matrix suction is reached. This latter scenario might occur when the TDR matrix suction sensor probe is pre-soaked in the liquid before it is inserted into the surrounding medium. Pre-soaking the probe can speed up the time required to reach equilibrium. For example, a probe pre-soaked in water prior to being inserted into soil may only take 15 minutes or less to equalize (assuming a 0.5 to 1.0 bar HN-CP jacket material), whereas a completely dry probe could take much longer. Then, if the liquid content of the media increases, additional liquid can flow from the media and be absorbed into the HN-CP jacket until the matrix suction exhibited by the media and the jacket material is re-equalized. Likewise, if the liquid content of the media decreases, liquid can flow from the HN-CP jacket and be absorbed back into the media until the matrix suction exhibited by the media and the jacket material is re-equalized. It is believed that this re-equalization will occur quickly. It is further noted that the TDR matrix suction sensor can generate pulses and compute the current matrix suction on an ongoing basis as equalization and re-equalization occurs. Equalization or re-equalization would be assumed to have occurred when the matrix suction does not change over several readings. This process can also be automated so that the medium can be continually monitored and any changes in its matrix suction can be automatically detected.

It is further noted that the choice of the HN-CP jacket material (and in particular its "bar" value) is dictated at least in part by the type of liquid to be exchanged. For example, while a 0.5 to 1.0 bar HN-CP jacket material is a good choice when the liquid is water, a higher bar value would be more appropriate for more viscous liquids. For instance, a 15.0 bar jacket would be a better choice for oil.

2.5 Other Advantages and Implementations

While the TDR matrix suction sensor has been described in more detail by specific reference to implementations thereof, it is understood that variations and modifications thereof can be made without departing from the true spirit and scope of the sensor. By way of example but not limitation, the matrix suction computing device of the TDR matrix suction sensor can be further configured to establish an indicator of whether liquid should be added to the porous medium surrounding the sensor based on the current value of the matrix suction exhibited by the porous medium. This liquid addition indicator can be provided to a user in addition to, or in lieu of, the previously described indicator of the current value of the matrix suction exhibited by the porous medium surrounding the sensor. As an example, it was previously indicated that the matrix suction associated with the range of matrix suction values representing the most energy efficient range for a plant is roughly −10 to −50 centibars. The matrix suction computing device of the TDR matrix suction sensor can be configured to direct a gardener to add water depending on the current matrix suction value sensed. For example, if the matrix suction is greater than about −50 centibars, the matrix suction computing device issues the liquid addition indicator.

Further, while up to this point the descriptions of the TDR matrix suction sensor implementations described herein have been directed to a stand-alone use in measuring porous materials, this need not be the case. Rather, a multi-sensor environment is possible. For instance, a plurality of TDR matrix suction sensors can be employed where each sensor is disposed at a different location within the porous medium so as to provide an analysis of the medium which covers a larger vertical and/or horizontal area. One example of such a scenario would be the use of the TDR matrix suction sensor implementations having a wireless transmission unit that transmits the matrix suction value associated with the porous medium in an area surrounding the sensor to a remote computing device. This remote computing device is configured to gather multiple matrix suction measurements from various locations and present it to a user. In another scenario, multiple TDR matrix suction sensors each include a wireless transmission unit that transmits either the computed delay time or the recorded pulse events to a centralized matrix suction computing device that computes the matrix suction exhibited by the media surrounding each of the TDR matrix suction sensors. In either scenario, the user would get a bigger picture of the conditions in porous medium across a larger area (vertically and/or horizontally) than would be possible using a single sensor.

It is further noted that any or all of the implementations that are described in the present document and any or all of the implementations that are illustrated in the accompanying drawings may be used and thus claimed in any combination desired to form additional hybrid implementations. In addition, although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What has been described above includes example implementations. It is, of course, not possible to describe every conceivable combination of components or methodologies for purposes of describing the claimed subject matter, but one of ordinary skill in the art may recognize that many further combinations and permutations are possible. Accordingly, the claimed subject matter is intended to embrace all such alterations, modifications, and variations that fall within the spirit and scope of the appended claims.

In regard to the various functions performed by the above described components, devices, circuits, systems and the like, the terms (including a reference to a "means") used to describe such components are intended to correspond, unless otherwise indicated, to any component which performs the specified function of the described component (e.g., a functional equivalent), even though not structurally equivalent to the disclosed structure, which performs the function in the herein illustrated exemplary aspects of the claimed subject matter. In this regard, it will also be recognized that the foregoing implementations include a system as well as a computer-readable storage media having computer-executable instructions for performing the acts and/or events of the various methods of the claimed subject matter.

There are multiple ways of realizing the foregoing implementations (such as an appropriate application programming interface (API), tool kit, driver code, operating system, control, standalone or downloadable software object, or the like), which enable applications and services to use the implementations described herein. The claimed subject matter contemplates this use from the standpoint of an API (or other software object), as well as from the standpoint of a software or hardware object that operates according to the implementations set forth herein. Thus, various implementations described herein may have aspects that are wholly in hardware, or partly in hardware and partly in software, or wholly in software.

The aforementioned systems have been described with respect to interaction between several components. It will be appreciated that such systems and components can include those components or specified sub-components, some of the specified components or sub-components, and/or additional components, and according to various permutations and combinations of the foregoing. Sub-components can also be implemented as components communicatively coupled to other components rather than included within parent components (e.g., hierarchical components).

Additionally, it is noted that one or more components may be combined into a single component providing aggregate functionality or divided into several separate sub-components, and any one or more middle layers, such as a management layer, may be provided to communicatively couple to such sub-components in order to provide integrated functionality. Any components described herein may also interact with one or more other components not specifically described herein but generally known by those of skill in the art.

3.0 Exemplary Operating Environments

Figure 6:
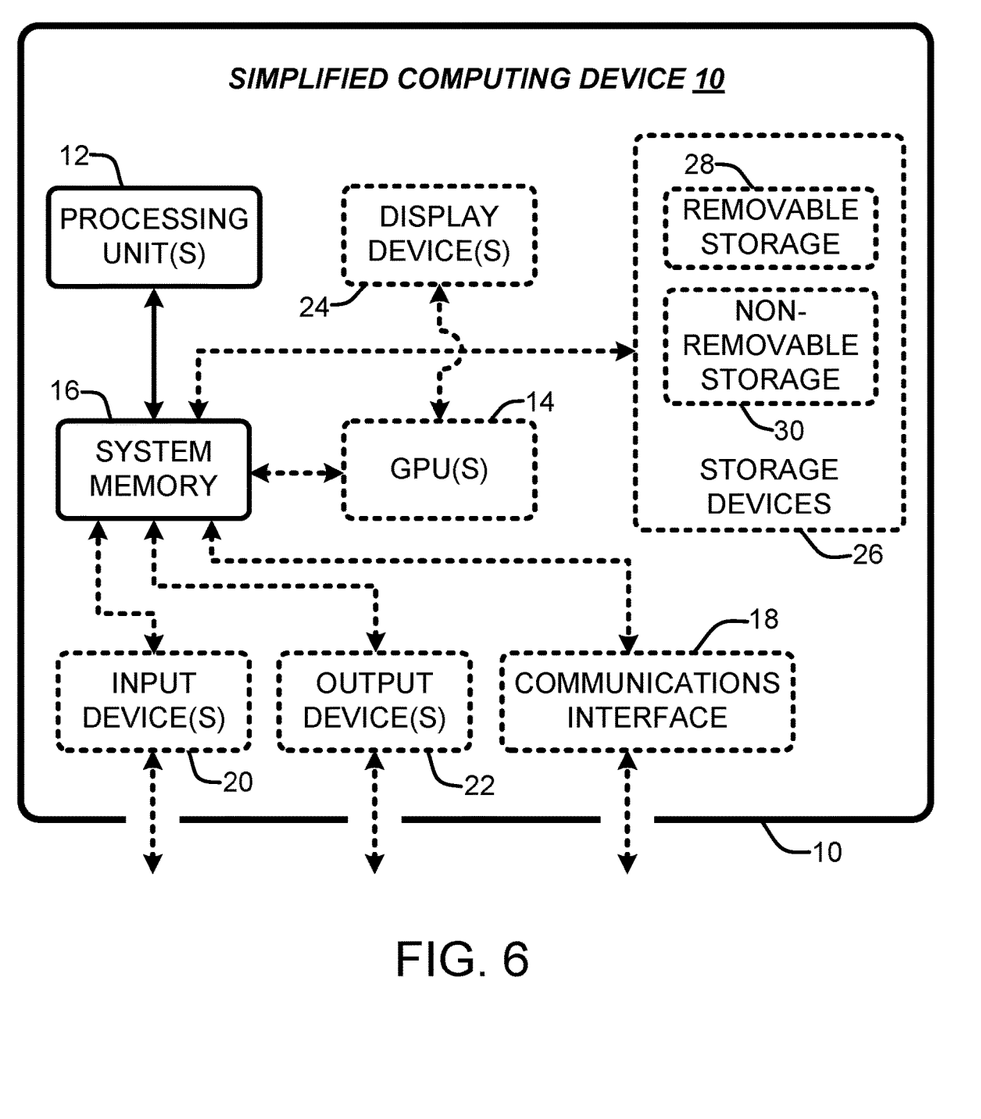
FIG. 6 is a diagram illustrating a simplified example of a general-purpose computer system on which various implementations and elements of the matrix suction computing device, as described herein, may be realized.

The TDR matrix suction sensor implementations described herein are operational within numerous types of general purpose or special purpose computing system environments or configurations. FIG. 6 illustrates a simplified example of a general-purpose computer system on which various implementations and elements of the TDR matrix suction sensor, as described herein, may be implemented. It is noted that any boxes that are represented by broken or dashed lines in the simplified computing device 10 shown in FIG. 6 represent alternate implementations of the simplified computing device. As described below, any or all of these alternate implementations may be used in combination with other alternate implementations that are described throughout this document. The simplified computing device 10 is typically found in devices having at least some minimum computational capability such as personal computers (PCs), server computers, handheld computing devices, laptop or mobile computers, communications devices such as cell phones and personal digital assistants (PDAs), multiprocessor systems, microprocessor-based systems, set top boxes, programmable consumer electronics, network PCs, minicomputers, mainframe computers, and audio or video media players.

To allow a device to realize the TDR matrix suction sensor implementations described herein, the device should have a sufficient computational capability and system memory to enable basic computational operations. In particular, the computational capability of the simplified computing device 10 shown in FIG. 6 is generally illustrated by one or more processing unit(s) 12, and may also include one or more graphics processing units (GPUs) 14, either or both in communication with system memory 16. Note that that the processing unit(s) 12 of the simplified computing device 10 may be specialized microprocessors (such as a digital signal processor (DSP), a very long instruction word (VLIW) processor, a field-programmable gate array (FPGA), or other micro-controller) or can be conventional central processing units (CPUs) having one or more processing cores.

In addition, the simplified computing device 10 may also include other components, such as, for example, a communications interface 18. The simplified computing device 10 may also include one or more conventional computer input devices 20 (e.g., touchscreens, touch-sensitive surfaces, pointing devices, keyboards, audio input devices, voice or speech-based input and control devices, video input devices, haptic input devices, devices for receiving wired or wireless data transmissions, and the like) or any combination of such devices.

Similarly, various interactions with the simplified computing device 10 and with any other component or feature of the TDR matrix suction sensor implementations described herein, including input, output, control, feedback, and response to one or more users or other devices or systems associated with the TDR matrix suction sensor implementations, are enabled by a variety of Natural User Interface (NUI) scenarios. The NUI techniques and scenarios enabled by the TDR matrix suction sensor implementations include, but are not limited to, interface technologies that allow one or more users user to interact with the TDR matrix suction sensor implementations in a "natural" manner, free from artificial constraints imposed by input devices such as mice, keyboards, remote controls, and the like.

Such NUI implementations are enabled by the use of various techniques including, but not limited to, using NUI information derived from user speech or vocalizations captured via microphones or other sensors (e.g., speech and/or voice recognition). Such NUI implementations are also enabled by the use of various techniques including, but not limited to, information derived from a user's facial expressions and from the positions, motions, or orientations of a user's hands, fingers, wrists, arms, legs, body, head, eyes, and the like, where such information may be captured using various types of 2D or depth imaging devices such as stereoscopic or time-of-flight camera systems, infrared camera systems, RGB (red, green and blue) camera systems, and the like, or any combination of such devices. Further examples of such NUI implementations include, but are not limited to, NUI information derived from touch and stylus recognition, gesture recognition (both onscreen and adjacent to the screen or display surface), air or contact-based gestures, user touch (on various surfaces, objects or other users), hover-based inputs or actions, and the like. Such NUI implementations may also include, but are not limited, the use of various predictive machine intelligence processes that evaluate current or past user behaviors, inputs, actions, etc., either alone or in combination with other NUI information, to predict information such as user intentions, desires, and/or goals. Regardless of the type or source of the NUI-based information, such information may then be used to initiate, terminate, or otherwise control or interact with one or more inputs, outputs, actions, or functional features of the TDR matrix suction sensor implementations described herein.

However, it should be understood that the aforementioned exemplary NUI scenarios may be further augmented by combining the use of artificial constraints or additional signals with any combination of NUI inputs. Such artificial constraints or additional signals may be imposed or generated by input devices such as mice, keyboards, and remote controls, or by a variety of remote or user worn devices such as accelerometers, electromyography (EMG) sensors for receiving myoelectric signals representative of electrical signals generated by user's muscles, heart-rate monitors, galvanic skin conduction sensors for measuring user perspiration, wearable or remote biosensors for measuring or otherwise sensing user brain activity or electric fields, wearable or remote biosensors for measuring user body temperature changes or differentials, and the like. Any such information derived from these types of artificial constraints or additional signals may be combined with any one or more NUI inputs to initiate, terminate, or otherwise control or interact with one or more inputs, outputs, actions, or functional features of the TDR matrix suction sensor implementations described herein.

The simplified computing device 10 may also include other optional components such as one or more conventional computer output devices 22 (e.g., display device(s) 24, audio output devices, video output devices, devices for transmitting wired or wireless data transmissions, and the like). Note that typical communications interfaces 18, input devices 20, output devices 22, and storage devices 26 for general-purpose computers are well known to those skilled in the art, and will not be described in detail herein.

The simplified computing device 10 shown in FIG. 6 may also include a variety of computer-readable media. Computer-readable media can be any available media that can be accessed by the computer 10 via storage devices 26, and can include both volatile and nonvolatile media that is either removable 28 and/or non-removable 30, for storage of information such as computer-readable or computer-executable instructions, data structures, programs, sub-programs, or other data. Computer-readable media includes computer storage media and communication media. Computer storage media refers to tangible computer-readable or machine-readable media or storage devices such as digital versatile disks (DVDs), blu-ray discs (BD), compact discs (CDs), floppy disks, tape drives, hard drives, optical drives, solid state memory devices, random access memory (RAM), read-only memory (ROM), electrically erasable programmable read-only memory (EEPROM), CD-ROM or other optical disk storage, smart cards, flash memory (e.g., card, stick, and key drive), magnetic cassettes, magnetic tapes, magnetic disk storage, magnetic strips, or other magnetic storage devices. Further, a propagated signal is not included within the scope of computer-readable storage media.

Retention of information such as computer-readable or computer-executable instructions, data structures, programs, sub-programs, and the like, can also be accomplished by using any of a variety of the aforementioned communication media (as opposed to computer storage media) to encode one or more modulated data signals or carrier waves, or other transport mechanisms or communications protocols, and can include any wired or wireless information delivery mechanism. Note that the terms "modulated data signal" or "carrier wave" generally refer to a signal that has one or more of its characteristics set or changed in such a manner as to encode information in the signal. For example, communication media can include wired media such as a wired network or direct-wired connection carrying one or more modulated data signals, and wireless media such as acoustic, radio frequency (RF), infrared, laser, and other wireless media for transmitting and/or receiving one or more modulated data signals or carrier waves.

Furthermore, software, programs, sub-programs, and/or computer program products embodying some or all of the various TDR matrix suction sensor implementations described herein, or portions thereof, may be stored, received, transmitted, or read from any desired combination of computer-readable or machine-readable media or storage devices and communication media in the form of computer-executable instructions or other data structures. Additionally, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, or media.

The TDR matrix suction sensor implementations described herein may be further described in the general context of computer-executable instructions, such as programs, sub-programs, being executed by a computing device. Generally, sub-programs include routines, programs, objects, components, data structures, and the like, that perform particular tasks or implement particular abstract data types. The TDR matrix suction sensor implementations may also be practiced in distributed computing environments where tasks are performed by one or more remote processing devices, or within a cloud of one or more devices, that are linked through one or more communications networks. In a distributed computing environment, sub-programs may be located in both local and remote computer storage media including media storage devices. Additionally, the aforementioned instructions may be implemented, in part or in whole, as hardware logic circuits, which may or may not include a processor. Still further, the TDR matrix suction sensor implementations described herein can be virtualized and realized as a virtual machine running on a computing device such as any of those described previously. In addition, multiple virtual machines can operate independently on the same computer device.

Alternatively, or in addition, the functionality described herein can be performed, at least in part, by one or more hardware logic components. For example, and without limitation, illustrative types of hardware logic components that can be used include FPGAs, application-specific integrated circuits (ASICs), application-specific standard products (ASSPs), system-on-a-chip systems (SOCs), complex programmable logic devices (CPLDs), and so on.

Wherefore, what is claimed is:

1. A time-domain reflectometry (TDR) matrix suction sensor for measuring the matrix suction exhibited by a porous medium, comprising:
    a TDR matrix suction sensor probe disposed within the porous medium, said probe comprising two or more elongated conductors and a jacket that encases the conductors, said jacket being made of a homogeneous hydrophilic, non-conductive, porous (HN-CP) material and whose exterior surface is in direct contact with the porous material;
    TDR electronics that are electrically connected to each probe conductor and which compute a pulse delay time for an electrical pulse injected into the proximal end of the probe conductors and reflected when reaching a distal end of the probe conductors; and
    a matrix suction computing device comprising one or more hardware-based processors, which is in communication with the TDR electronics, and a matrix suction measuring computer program having a plurality of sub-programs executable by said matrix suction computing device, wherein the sub-programs configure said matrix suction computing device to,
        compute the matrix suction exhibited by the probe jackets based on the computed pulse delay time and a delay-to-matrix suction profile which defines the relationship between a pulse delay time value and the matrix suction exhibited by the HN-CP material of the probe jacket, and
        establish an indicator of the current value of the matrix suction exhibited by the porous medium based on the computed matrix suction exhibited by the HN-CP material of the probe jackets.

2. The TDR matrix suction sensor of claim 1, wherein the TDR electronics and matrix suction computing device are part of the same integrated unit.

3. The TDR matrix suction sensor of claim 1, wherein the TDR electronics are directly connected to the matrix suction computing device via a wired connection.

4. The TDR matrix suction sensor of claim 1, wherein the HN-CP material employed in the jacket exhibits a continuous, interconnected system of pores which is permeable to liquids, gasses and combinations thereof, and wherein the pores have a known distribution throughout, and a known size distribution.

5. The TDR matrix suction sensor of claim 1, wherein the HN-CP material employed in the jacket is one of a porous ceramic material or a porous plastic material.

6. The TDR matrix suction sensor of claim 1, wherein the jacket comprises interior cavities each of which accommodates and conforms to the shape of a different one of the probe conductors such that the walls of each jacket cavity contacts the conductor across its exterior surface without forming any significant gaps where liquid could pool.

7. The TDR matrix suction sensor of claim 1, wherein the exterior of the jacket has a radial cross-sectional circular shape with a dome-shaped or conical-shaped distal end.

8. The TDR matrix suction sensor of claim 1, wherein the exterior of the jacket has a radial cross-sectional shape forming a rectangle, or a square, or a triangular, or an oval, or a pentagon, or a hexagon, or an octagon, or a star.

9. The TDR matrix suction sensor of claim 8, wherein the distal end of the exterior of the jacket has a pointed shape.

10. The TDR matrix suction sensor of claim 1, wherein the matrix suction computing device further establishes an indicator of whether liquid should be added to the porous medium surrounding the sensor based on the current value of the matrix suction exhibited by the porous medium.

11. A time-domain reflectometry (TDR) matrix suction sensor for measuring the matrix suction exhibited by a porous medium, comprising:
    a TDR matrix suction sensor probe disposed within the porous medium, said probe comprising two or more elongated conductors and a jacket that encases the conductors, said jacket being made of a homogeneous hydrophilic, non-conductive, porous (HN-CP) material and whose exterior surface is in direct contact with the porous material;
    TDR electronics that are electrically connected to a proximal end of each probe conductor and which injects an initial electrical pulse into the proximal end of the probe conductors and records the time of injection, and which detects the arrival of a reflected pulses generated when the initial pulse is reflected upon reaching a distal end of the probe conductors and records the time of arrival; and a matrix suction computing device comprising one or more hardware-based processors, which is in communication with the TDR electronics, and a matrix suction measuring computer program having a plurality of sub-programs executable by said matrix suction computing device, wherein the sub-programs configure said matrix suction computing device to, compute a pulse delay time based on the injection time of the initial pulse and the arrival time of the reflected pulses, compute the matrix suction exhibited by the probe jackets based on the computed pulse delay time and a delay-to-matrix suction profile which defines the relationship between a pulse delay time value and the matrix suction exhibited by the HN-CP material of the probe jacket, and establish an indicator of the current value of the matrix suction exhibited by the porous medium based on the computed matrix suction exhibited by the HN-CP material of the probe jackets.

12. The TDR matrix suction sensor of claim 11, wherein the matrix suction computing device is in a remote location separate from the TDR electronics, and in communication with the TDR electronics via a wireless connection.

13. The TDR matrix suction sensor of claim 11, wherein the HN-CP material employed in the jacket exhibits a continuous, interconnected system of pores which is permeable to liquids, gasses and combinations thereof, and wherein the pores have a known distribution throughout, and a known size distribution.

14. The TDR matrix suction sensor of claim 11, wherein the HN-CP material employed in the jacket is one of a porous ceramic material or a porous plastic material.

15. The TDR matrix suction sensor of claim 11, wherein the jacket comprises interior cavities each of which accommodates and conforms to the shape of a different one of the probe conductors such that the walls of each jacket cavity contacts the conductor across its exterior surface without forming any significant gaps where liquid could pool.

16. The TDR matrix suction sensor of claim 11, wherein the exterior of the jacket has a radial cross-sectional circular shape with a dome-shaped or conical-shaped distal end.

17. The TDR matrix suction sensor of claim 11, wherein the exterior of the jacket has a radial cross-sectional shape forming a rectangle, or a square, or a triangular, or an oval, or a pentagon, or a hexagon, or an octagon, or a star.

18. The TDR matrix suction sensor of claim 17, wherein the distal end of the exterior of the jacket has a pointed shape.

19. The TDR matrix suction sensor of claim 11, wherein the matrix suction computing device further establishes an indicator of whether liquid should be added to the porous medium surrounding the sensor based on the current value of the matrix suction exhibited by the porous medium.

20. A computer-implemented process for measuring the matrix suction exhibited by a porous medium, comprising the actions of:

using one or more computing devices each of which comprises one or more hardware-based processors, that are in communication with each other to perform the following process actions:

injecting an initial electrical pulse into conductors at a proximal end of a TDR matrix suction sensor probe disposed within the porous medium, said probe comprising two or more elongated conductors and a jacket that encases the conductors, said jacket being made of a homogeneous hydrophilic, non-conductive, porous (HN-CP) material and whose exterior surface is in direct contact with the porous material;

recording the time the initial electrical pulse was injected;

detecting the arrival of reflected electrical pulses generated when the initial pulse is reflected upon reaching a distal end of the probe conductors;

recording the time of arrival of the reflected electrical pulses;

computing a pulse delay time based on the injection time of the initial pulse and the arrival time of the reflected pulses;

computing the matrix suction exhibited by the HN-CP material of the probe jackets based on the pulse delay time and a delay-to-matrix suction profile which defines the relationship between a delay and the matrix suction exhibited by the HN-CP probe material; and establishing an indicator of the current value of the matrix suction exhibited by the porous medium based on the matrix suction computed for the HN-CP material of the probe jackets.

* * * * *